(12) United States Patent
Ritter et al.

(10) Patent No.: US 8,404,898 B2
(45) Date of Patent: Mar. 26, 2013

(54) INTEGRATED PROCESS FOR THE PREPARATION OF POLYBENZIMIDAZOLE PRECURSORS

(75) Inventors: Joachim C. Ritter, Wilmington, DE (US); Rajiv Dhawan, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 604 days.

(21) Appl. No.: 12/634,734

(22) Filed: Dec. 10, 2009

(65) Prior Publication Data

US 2010/0160685 A1    Jun. 24, 2010

Related U.S. Application Data

(60) Provisional application No. 61/138,615, filed on Dec. 18, 2008.

(51) Int. Cl.
*C07C 209/38* (2006.01)
(52) U.S. Cl. ...................................... 564/406
(58) Field of Classification Search .................. 564/406
See application file for complete search history.

(56) References Cited

U.S. PATENT DOCUMENTS

| | | | |
|---|---|---|---|
| 3,476,590 A | 11/1969 | Rabilloud et al. | |
| 3,783,137 A | 1/1974 | Gerber | |
| 8,188,316 B2 * | 5/2012 | Dhawan et al. | 564/441 |
| 8,188,317 B2 * | 5/2012 | Dhawan et al. | 564/441 |

FOREIGN PATENT DOCUMENTS

| | | |
|---|---|---|
| JP | 2003292476 | 10/2003 |
| JP | 2005330470 | 12/2005 |
| JP | 2005330471 | 12/2005 |

OTHER PUBLICATIONS

Ritter et al., U.S. Appl. No. 12/634,730, filed Dec. 10, 2009.
Blanksma, Nitro Derivatives of 2,6-Dibromotoluene, Chemisch Weekblad, 1913, vol. 9, pp. 968-973, Abstract Only.
Cotton and Wilkinson, Advanced Inorganic Chemistry, Periodic Table Only, 1966, Interscience Publishers, 2nd Edition, New York.

\* cited by examiner

*Primary Examiner* — Yong Chu
(74) *Attorney, Agent, or Firm* — Kevin S. Dobson

(57) ABSTRACT

An integrated process is provided for preparing 2,3,5,6-tetraminotoluene and salts thereof starting with nitration of 2,6-dihalotoluene. The process design eliminates costly intermediate drying and recrystallization steps. Handling of solid materials with possible skin sensitizing properties and toxicity is avoided, thereby eliminating human and environmental exposure.

8 Claims, 1 Drawing Sheet

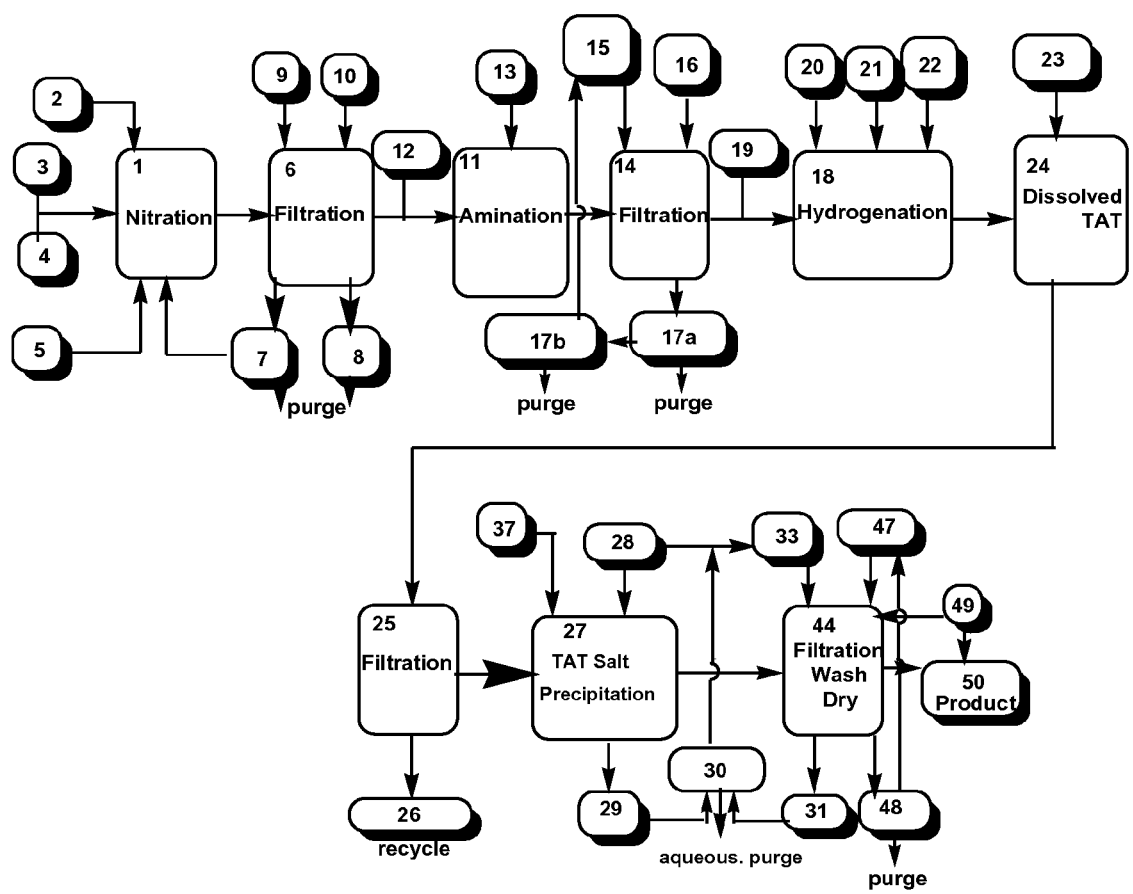

INTEGRATED PROCESS FOR THE PREPARATION OF POLYBENZIMIDAZOLE PRECURSORS

This application claims priority under 35 U.S.C. §119(e) from, and claims the benefit of, U.S. Provisional Application No. 61/138,615, filed Dec. 18, 2008, which is by this reference incorporated in its entirety as a part hereof for all purposes.

TECHNICAL FIELD

The disclosure relates to methods of making 2,3,5,6-tetraminotoluene and salts thereof, which are then used to make high-performance polybenzimidazole polymers.

BACKGROUND

The synthesis of preferred polybenzimidazole based high performance fibers requires the selective polymerization of 2,3,5,6-tetraminotoluene ("TAT") with various substituted and unsubstituted aromatic diacids, such as 2,5-dihydroxyterephthalic acid ("DHTA").

TAT has been mentioned in the literature (e.g., U.S. Pat. Nos. 3,476,590 and 3,783,137) as a comonomer in the synthesis of polybenzarenazole polymers. TAT can be used as a crosslinking comonomer using radical induced crosslinking at the methyl group. For example, in Japanese Patent Application 2005-330470A, TAT is used as a crosslinking comonomer in the synthesis of a polybenzimidazole polymer for film applications. However, none of these references discloses a source or synthesis for TAT.

There remains a need for a process for the safe and efficient production of high-purity 2,3,5,6-tetraminotoluene (TAT) and salts of 2,3,5,6-tetraminotoluene that can be converted to 2,3,5,6-tetraminotoluene, to make an aromatic diacid complex of 2,3,5,6-tetraminotoluene of high enough purity for use in making a high molecular weight polymer material for producing high-performance fibers. For reasons of cost and safety it would be highly desirable to have a process where intermediates do not need to be isolated as dry materials.

SUMMARY

In one embodiment, this invention provides an integrated process for preparing 2,3,5,6-tetraminotoluene or a 2,3,5,6-tetraminotoluene salt comprising the sequential steps under exclusion of oxygen:
a) nitrating 2,6-dihalotoluene (II)

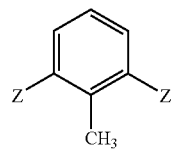

II wherein each Z is independently Cl or Br, in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene;
(iii) the concentration of 2,6-dihalotoluene in the reaction mixture is between about 12 and about 24 weight percent; and
wherein the temperature of the reaction mixture does not exceed 120° C.;
thereby producing 2,6-dihalo-3,5-dinitrotoluene;
b) directly separating the 2,6-dihalo-3,5-dinitrotoluene from the reaction mixture by filtration, while recycling the sulfuric acid mother liquor;
c) washing the 2,6-dihalo-3,5-dinitrotoluene with water or acid then water, then with $NH_4OH$, and then mixing it with glycol as a suspension;
d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene;
e) directly separating the 2,6-diamino-3,5-dinitrotoluene from the reaction mixture by filtration, washing with glycol, then washing with water;
f) forming a slurry of the 2,6-diamino-3,5-dinitrotoluene with water and transferring the slurry to a hydrogenation reactor containing a hydrogenation catalyst to form a reaction mixture;
g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraminotoluene;
h) contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;
i) filtering the reaction mixture, thereby removing the spent hydrogenation catalyst;
j) forming and precipitating the salt by adding an acid to the filtered reaction mixture; and
k) cooling, filtering, and washing the precipitated 2,3,5,6-tetraminotoluene salt.

BRIEF DESCRIPTION OF THE DRAWINGS

The invention is illustrated by way of example and not limitation in the accompanying figures.

FIG. 1 is a schematic representation of an embodiment of the process described herein.

DETAILED DESCRIPTION

The following description is exemplary and explanatory only and is not restrictive of the invention, as defined in the appended claims.

An integrated process is provided for preparing 2,3,5,6-tetraminotoluene (I)

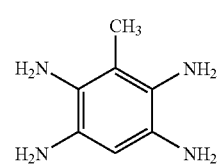

I or a 2,3,5,6-tetraminotoluene salt comprising the sequential steps under exclusion of oxygen:

a. nitrating 2,6-dihalotoluene (II)

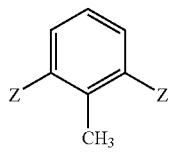

wherein each Z is independently Cl or Br, in a reaction mixture comprising oleum or $SO_3$, nitric acid, and $H_2SO_4$
wherein
(i) the concentration of nitric acid is about 2.0 to about 2.3 moles per mole of 2,6-dihalotoluene;
(ii) the concentration of $SO_3$ is about 1 to about 3 moles per mole of 2,6-dihalotoluene;
(iii) the concentration of 2,6-dihalotoluene in the reaction mixture is between about 12 and about 24 weight percent; and
wherein the temperature of the reaction mixture does not exceed 120° C.; thereby producing 2,6-dihalo-3,5-dinitrotoluene;
b. directly separating the 2,6-dihalo-3,5-dinitrotoluene from the reaction mixture by filtration, while recycling the sulfuric acid mother liquor;
c. washing the 2,6-dihalo-3,5-dinitrotoluene with water or acid then water, then with $NH_4OH$, and then mixing it with glycol as a suspension;
d. aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene
e. directly separating the 2,6-diamino-3,5-dinitrotoluene from the reaction mixture by filtration, washing with glycol, then washing with water,
f. forming a slurry of the 2,6-diamino-3,5-dinitrotoluene with water and transferring the slurry to a hydrogenation reactor containing a hydrogenation catalyst to form a reaction mixture;
g. hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraminotoluene;
h. contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;
i. filtering the reaction mixture, thereby removing the spent hydrogenation catalyst;
j. forming and precipitating the 2,3,5,6-tetraminotoluene salt by adding an acid to the filtered reaction mixture; and
k. cooling, filtering, and washing the precipitated 2,3,5,6-tetraminotoluene salt.

In the context of this disclosure, a number of terms shall be utilized.

As used herein, the term "TAT salt" or, equivalently, "2,3,5,6-tetraminotoluene salt," denotes a compound formed by reaction of 2,3,5,6-tetraminotoluene with an acid such as HCl, acetic acid, $H_2SO_4$, or $H_3PO_4$. One example of a TAT salt is TAT.4HCl.

As used herein, the term "XYTA" denotes 2-X-5-Y-terephthalic acid, where X and Y each independently selected from the group consisting of H, OH, SH, methyl, ethyl, F, Cl, and Br. One example is 2,5-dihydroxyterephthalic acid, in which X=Y=OH. The disodium or dipotassium salt of the diacid is represented by the term "$M_2XYTA$" where M is Na or K.

As used herein, the term "oleum" denotes fuming sulfuric acid, which is anhydrous and is formed by dissolving excess sulfur trioxide ($SO_3$) into sulfuric acid.

As used herein, the term "fuming nitric acid" denotes concentrated nitric acid containing dissolved nitrogen dioxide.

As used herein, the term "net yield" of P denotes the actual, in-hand yield, i.e., the theoretical maximum yield minus losses incurred in the course of activities such as isolating, handling, drying, and the like.

As used herein, the term "purity" denotes what percentage of an in-hand, isolated sample is actually the specified substance.

The process is designed in such a way that solids handling is avoided. Filtered materials are transferred, without prior drying, in the form of suspension slurries in the solvent that is used for the respective reaction step. This process design thereby avoids costly drying processes. It also avoids the handling of solid materials with possible skin sensitizing properties and toxicity, and eliminates human and environmental exposure to them.

One embodiment of the process described here is illustrated in FIG. 1; possible minor modifications will be evident to one skilled in the art. With reference to the embodiment shown schematically in FIG. 1, the process starts with the nitration 1 of 2,6-dihalotoluene (i.e., 2,6-dichlorotoluene, 2,6-dibromotoluene, or 2-bromo-6-chlorotoluene; 2,6-dichlorotoluene is preferred), in a reaction mixture prepared by combining the 2,6-dihalotoluene 2; sulfuric acid; oleum 3 or $SO_3$ 5; and nitric acid 4. The concentration of nitric acid is about 2.0 to about 2.3 moles per mole of 2,6-dihalotoluene. Concentrated nitric acid (e.g., commonly used reagent grade, which is about 70% nitric acid in water) can be used, but fuming nitric acid is preferred. If concentrated nitric acid is used, since in the process described herein water must be kept at a level below one equivalent to get highly pure product, more $SO_3$ would be added to remove the water from the nitric acid (by reacting with it to form sulfuric acid) and still have sufficient $SO_3$ present in the reaction mixture for the nitration reaction. The concentration of $SO_3$ is about 1 to about 3 moles, preferably 1.5 to 2 moles, per mole of 2,6-dihalotoluene. The sulfuric acid is present in an amount such that the weight percent of 2,6-dihalotoluene in the reaction mixture (i.e., the weight of 2,6-dihalotoluene relative to the combined weight of 2,6-dihalotoluene plus the acid solution) is between 12 and 24 weight percent.

The nitration reaction is carried out at a temperature not to exceed about 120° C., typically in the range of about 5° C. to about 100° C., preferably in the range of about 5° C. to about 40° C., and more preferably in the range of about 5° to about 15° C. The 2,6-dihalo-3,5-dinitrotoluene thereby produced is separated directly by filtration 6 from the reaction mixture as a crude crystal cake without quench or recrystallization steps. The crude crystal cake is washed (9, 10) with water or with acid (e.g., concentrated or dilute sulfuric acid) then water; and is then washed with $NH_4OH$. Aqueous waste is discarded 8. The sulfuric acid mother liquor is recycled 7, 1 with a purge drawn to prevent excess sulfuric acid accumulation. The resulting wet cake of 2,6-dihalo-3,5-dinitrotoluene is then mixed with glycol 12 and introduced into the amination reactor 11 as a suspension.

The suspension is heated to a temperature in the range of about 100° C. to about 160° C., preferably about 140° C., to dissolve the 2,6-dihalo-3,5-dinitrotoluene in the glycol. The resulting solution is contacted at that temperature with gaseous NH$_3$ 13 for approximately four to eight hours close to ambient pressure; the NH$_3$ is fed as it is consumed. At reaction completion, the 2,6-diamino-3,5-dinitrotoluene thereby produced is filtered 14, typically at about 60° C., and washed with glycol 15 and then water 16. The mother liquor (filtrate) containing glycol is collected 17a, and the glycol is distilled and recycled 17b, 15; purges are drawn to prevent accumulation. The wet cake of 2,6-diamino-3,5-dinitrotolueneis slurried with water 19 and transferred to the hydrogenation reactor 18 as a suspension.

The hydrogenation reactor also contains a hydrogenation catalyst 22. Examples of suitable hydrogenation catalysts include without limitation Pd/C and Pt/C and mixtures thereof, optionally containing other metals from Groups VIII through X such as Fe. The groups are as described in the Periodic Table in *Advanced Inorganic Chemistry* by F. A. Cotton and G. Wilkinson, Interscience New York, 2nd Ed. (1966). Of these, Pt/C is preferred. The catalyst is typically used in the amount of about 0.5 to about 5.0 wt % metal based on 2,6-diamino-3,5-dinitrotoluene.

The hydrogenation reactor is purged with nitrogen, and the aqueous suspension is contacted with hydrogen 21 in the presence of about 0 to about 1 mol equivalent of NH$_{3(g)}$ 20 to form a reaction mixture. The reaction is carried out at a temperature in the range of about to 20° C. to 100° C., preferably about 60° C. to about 85° C., and a hydrogen pressure of about 45 to about 500 psi (0.31 to 3.45 MPa) preferably about 300 psi (2.07 MPa). Reaction continues for a time sufficient to consume about 6 to 7 mol equivalents of hydrogen, thereby producing 2,3,5,6-tetraminotoluene ("TAT"). The time required depends on the details of the specific set up but is typically about 2 hours.

As shown in FIG. 1, about 1 to up to about 5 equivalents, preferably about 1 to about 4 equivalents, of an acid 23 are added to dissolve the TAT; as a result, a soluble acid salt of TAT is formed, herein referred to as "TAT salt." Among the acids, HCl is preferred, and the TAT salt generally prepared is TAT.4HCl. The solution may be heated to facilitate dissolution. Optionally, a co-solvent may be present. Examples of co-solvents include without limitation methanol, ethanol, and isopropanol. Optionally, the solution may be filtered through an adsorbent material capable of adsorbing impurities. Examples of adsorbent materials include without limitation active carbon, alumina and microporous styrene.

The resulting reaction mixture 24 is then filtered 25, typically at a temperature in the range of about 60° C. to about 80° C., to remove the spent hydrogenation catalyst 26, preferably by passing through a carbon filter bed. The spent catalyst can then be recycled.

The filtered reaction mixture (or "filtrate") is a TAT salt solution and can be treated in either of two ways. To make TAT directly, a base (e.g., sodium hydroxide) is added to the filtrate.

Alternatively, as in the embodiment shown in FIG. 1, acid is added 28 at a temperature in the range of about 10° C. to about 80° C. to form and precipitate the TAT salt 27, for example, TAT.4HCl. The amount of acid needed for this step will depend on the concentration of TAT in the filtrate and is readily determined by one skilled in the art. Typically, about 6 to about 8 equivalents of acid (as for example, 38% HCl$_{aq}$) are needed in this step to precipitate the TAT salt (for example, as TAT.4HCl) in about 90% yield. The use of gaseous acid, such as gaseous HCl, might reduce the total volume of liquid needed since the additional introduction of water with aqueous acid in both addition steps increases the absolute solubility of the TAT salt in the filtered reaction mixture. The addition of equivalent amounts of acid in the gas phase instead of as an aqueous solution (for example, HCl$_{gas}$ instead of HCl$_{aq}$) may be also desirable since the liquid volumes are thereby reduced, and crystallization yields are expected to be higher as a consequence. More commonly, however, aqueous acid (for example, 30-38 wt % HCl) is used because it is easier to handle than the acid in the gas phase. Aqueous acid can be recovered 29, distilled 30, and recycled (30, 28) or used in the acid wash step of the process (30, 33, 44).

To facilitate the precipitation of the TAT salt (for example, as TAT.4HCl) an aliphatic alcohol co-solvent may optionally be added. Examples of suitable alcohol co-solvents included without limitation: methanol, ethanol, n-propanol, and isopropanol.

A small amount of tin (e.g., about 0.5% tin powder) is optionally added 37 to reduce impurities caused by oxidation and to prevent further impurity formation by that route.

The reaction mixture containing the precipitated TAT salt is then cooled to about 5° C. to about 15° C. and stirred, then filtered. The TAT salt is then washed 44. It may be washed with deaerated aqueous acid, such as HCl (33%), and then optionally with deaerated ethanol or methanol to produce a wet cake material; the optional ethanol or methanol wash can then be recycled as shown in FIG. 1 48, 47 and a purge is drawn to prevent accumulation. Using an agitated filter unit during the wash procedures can allow for a reduction of the wash volumes. Under such circumstances, using small amounts of cold (e.g., about 5° C.) water instead of the aqueous acid would be effective; cold water would be used because of lower solubility of the TAT salt in cold water versus, e.g., room temperature. For example, the solubility of TAT.4HCl in water at 25° C. is about 16 wt %.

Whether aqueous acid or cold water is used as a wash, it may be possible to eliminate the ethanol or methanol wash and dry directly from aqueous wet cake or simply use the wet cake in subsequent processing. It is likely that in a commercial process one would only wash with HCl$_{aq}$ and, if desired, dry directly.

The resulting wet cake material (TAT salt) can be used in subsequent processing without drying or can be dried, as in FIG. 1 44, for example at a pressure less than 400 Torr and a temperature of about 30° C. to about 50° C., under a stream of N$_2$ 49. The dried product 50 is preferably kept under nitrogen.

The yield of TAT salt can be increased by recovered additional TAT salt from the filtrate remaining from the reaction mixture that contained the precipitated TAT salt (i.e., the "mother liquor") by, e.g., evaporation of water.

Oxygen is excluded throughout all steps of the process of making the TAT salt. Deaerated water and deaerated acid are used.

The process described herein is an efficient and effective way to produce high purity TAT salts, such as TAT.4HCl, which are precursors for making polybenzimidazole polymer for high performance fibers. This process design eliminates costly intermediate drying and recrystallization steps. The recycling of spent catalyst, acids, glycol, and methanol contributes economical and environmental advantages. And, importantly, handling of solid materials with possible skin sensitizing properties and toxicity is avoided, thereby eliminating human and environmental exposure.

The materials, methods, and examples herein are illustrative only and, except as specifically stated, are not intended to be limiting.

EXAMPLES

The present invention is further defined in the following examples. It should be understood that these examples, while indicating preferred embodiments of the invention, are given by way of illustration only. From the above discussion and these examples, one skilled in the art can ascertain the essential characteristics of this invention, and without departing from the spirit and scope thereof, can make various changes and modifications of the invention to adapt it to various uses and conditions.

All water used was deaerated and de-ionized water. The examples were carried out under exclusion of oxygen.

The meaning of abbreviations is as follows: "d" means density, "DADNT" means 2,6-diamino-3,5-dinitrotoluene, "DCDNT" means 2,6-dichloro-3,5-dinitrotoluene, "equiv" means equivalent(s), "g" means gram(s), "gal" means gallon, "GC" means gas chromatography, "$^1$H-NMR" means proton nuclear magnetic resonance spectroscopy, "h" means hour(s), "L" means liter(s), "mL" means milliliter(s), "mol" means mole(s), "MPa" means megapascals, and "psi" means pounds per square inch.

Example 1

Preparation of DCDNT

To a 1 L 3-neck round bottom flask equipped with external ice cooling, mechanical stirrer, addition funnel, $N_2$ inlet, and thermometer was added 174 g (2.76 mol) fuming nitric acid (d=1.54), followed by 350 g sulfuric acid and 659 g 30% oleum (2.0 molar equiv $SO_3$) maintaining a temperature between 5 and 20 C. Subsequently, 199 g (1.23 mol) 1,3-dichlorotoluene (99% purity, Aldrich Chemical Company, Milwaukee, Wis., USA) was added over a time period of 3 h while maintaining a temperature between 0° C.-10° C. The ice bath was removed, and the reaction mixture was allowed to warm up to room temperature. It was then heated to 100° C. for about 2 h. To analyze the reaction mixture, a small sample of crude product was taken from the reaction vessel and poured into ice water. The crude product was extracted with methylene chloride. Analysis by GC indicated a reaction selectivity to 3,5-dinitro-2,6-dichlorotoluene of >97%. Subsequently, the reaction mixture was allowed to cool to room temperature over 2 h and then cooled to 5° C. over 30 min, after which it was filtered through a glass fritted funnel and washed with a little sulfuric acid followed by 200 mL $H_2O$. The wet cake contained about 20% water. After drying, 291 g of >99.5% pure DCDNT product (by $^1$H-NMR) was isolated (93.5% net yield).

Example 2

Larger-Scale Preparation of DCDNT

This example was carried out in a similar fashion as described in Example 1 but on a larger scale, using 3500 g 2,6-dichlorotoluene, 2807.6 g fuming nitric acid (d=1.54) and 17826.0 g oleum (20%) in a 22 L glass reactor. After washing with sulfuric acid and water the wet cake was isolated and processed directly in Example 3. The net yield of 2,6-dichlorotoluene was 90.6% and the purity was 99.2%.

Example 3

Preparation of DADNT from DCDNT

To a 22-L 4-neck Morton style round bottom glass reaction vessel equipped with external ice cooling, mechanical stirrer, addition funnel, $N_2$ inlet and outlet, and thermometer was added DCDNT wet cake (approximately 9.2 mol, 1 equiv) in 14.5 L ethylene glycol at room temperature, forming a yellow slurry. The reaction vessel was purged with nitrogen while heating the yellow slurry to 150° C. When the reaction temperature reached about 120° C., the mixture became a greenish-yellow solution. After reaching 145° C.-150° C., ammonia addition was begun. A total of 1000 g ammonia (58.32 mol, 6.38 equiv) was added over 9.5 hours.

The reaction slurry was cooled to 60° C.-65° C., filtered, and washed successively with warm (60° C.) ethylene glycol (2×1000 mL), water (2×1000 mL) and the water is removed by suction. The resulting wet cake contained about 12% water and could be used directly in Example 4. The wet cake contained approximately 1900 g of bronze colored solids of 96% purity, by GC. For a dry product the wet cake could be washed with methanol (3×1000 mL) and dried under $N_2$ overnight.

Example 4

Preparation of TAT.4HCl from DADNT Wet Cake

A 1 gal (3.79 L) stirred Hastelloy autoclave was charged with 547 g of DADNT wet cake (480 g DADNT, 67 g water) prepared in Example 3 and 9.6 g of 5% Pt/C (dry basis 5% Pt on C catalyst, wetted with 50% water, Degussa F101, obtained from Degussa, now Evonik Degussa, a subsidiary of Evonik Industries AG, Essen, Germany). The autoclave was purged 5 times with $N_2$ and 2 times with $H_2$ at 90 psi (0.62 MPa). Subsequently, 2200 mL of deaerated water (purged with $N_2$ overnight) were added and the mixture was pressurized at 81° C. to 300 psi (2.07 MPa). Hydrogenation was continued for a total time of about 3 h with an approximate uptake of 16 moles of $H_2$ (6.5 equiv). The excess hydrogen was released and the autoclave was cooled to 40° C. and purged twice with $N_2$, after which 489 g of deaerated $HCl_{aq}$ (36.3%, by titration) was added. The mixture was stirred and heated back up to 80° C., then passed through a carbon bed filter at about 65° C. to remove catalyst and a small amount of unconverted starting material. The autoclave was rinsed with 300 mL of deaerated water at 80° C. The combined solutions were directly charged into a stirred vessel, about 5 g of Sn powder was added, and at 70° C. 1400 mL of deaerated $HCl_{aq}$ (38%, about 6 equiv) was added over a time period of 15 min with vigorous stirring. The white precipitate TAT.4HCl formed while the pH dropped from 3.5 to 0.9. After completion of the precipitation, the mixture was cooled to 10° C. and stirred for 15 min before it was filtered through a glass frit and washed twice with 250 mL deaerated $HCl_{aq}$ (33%) and twice with 250 mL deaerated ethanol. The resulting wet cake material (TAT.4HCl salt) was dried at a pressure under 400 Torr and a temperature of 30° C.-50° C. under a stream of $N_2$, using a heating mantel around the filter unit set at 40° C. Vacuum was pulled at the bottom of the unit and a stream of $N_2$ was supplied to the top of the unit, maintaining a positive pressure above the filter.

The net yield was 650 g, 93% based on the net amount of 2,6-diamino-3,5-dinitrotoluene starting material. A remainder of 5% mol equivalents was recovered from the mother liquor as TAT.4HCl, increasing the net yield to 98%.

It is to be appreciated that certain features of the invention which are, for clarity, described above and below in the context of separate embodiments, may also be provided in combination in a single embodiment. Conversely, various features of the invention that are, for brevity, described in the context of a single embodiment, may also be provided separately or in any subcombination. Further, reference to values stated in ranges includes each and every value within that range.

Unless otherwise defined, all technical and scientific terms used herein have the same meaning as commonly understood by one of ordinary skill in the art to which this invention belongs. In case of conflict, the present specification, including definitions, will control.

Although methods and materials similar or equivalent to those described herein can be used in the practice or testing of the present invention, suitable methods and materials are described herein.

Unless stated otherwise, all percentages, parts, ratios, etc., are by weight.

When an amount, concentration, or other value or parameter is given as either a range, preferred range or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

When the term "about" is used in describing a value or an end-point of a range, the disclosure should be understood to include the specific value or end-point referred to.

As used herein, the terms "comprises," "comprising," "includes," "including," "containing," "characterized by," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Use of "a" or "an" are employed to describe elements and components of the invention. This is done merely for convenience and to give a general sense of the invention. This description should be read to include one or at least one and the singular also includes the plural unless it is obvious that it is meant otherwise.

What is claimed is:

1. An integrated process for preparing 2,3,5,6-tetraaminotoluene or a 2,3,5,6-tetraminotoluene salt comprising the sequential steps under exclusion of oxygen:
    a) nitrating 2,6-dihalotoluene (II)

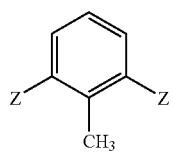

wherein each Z is independently Cl or Br, in a reaction mixture comprising oleum or $SO_3$, nitric acid, and $H_2SO_4$
    wherein
        (iv) the concentration of nitric acid is about 2.0 to about 2.3 moles per mole of 2,6-dihalotoluene;
        (v) the concentration of $SO_3$ is about 1 to about 3 moles per mole of 2,6-dihalotoluene;
        (vi) the concentration of 2,6-dihalotoluene in the reaction mixture is between about 12 and about 24 weight percent; and
    wherein the temperature of the reaction mixture does not exceed 120° C.;
    thereby producing 2,6-dihalo-3,5-dinitrotoluene;
    b) directly separating the 2,6-dihalo-3,5-dinitrotoluene from the reaction mixture by filtration, while recycling the sulfuric acid mother liquor;
    c) washing the 2,6-dihalo-3,5-dinitrotoluene with water or acid then water, then with $NH_4OH$, and then mixing it with glycol as a suspension;
    d) aminating the 2,6-dihalo-3,5-dinitrotoluene by heating the suspension formed in step (c) to a temperature in the range of about 100° C. to about 160° C. and contacting it with $NH_{3(g)}$, thereby converting the 2,6-dihalo-3,5-dinitrotoluene to 2,6-diamino-3,5-dinitrotoluene
    e) directly separating the 2,6-diamino-3,5-dinitrotoluene from the reaction mixture by filtration, washing with glycol, then washing with water,
    f) forming a slurry of the 2,6-diamino-3,5-dinitrotoluene with water and transferring the slurry to a hydrogenation reactor containing a hydrogenation catalyst to form a reaction mixture;
    g) hydrogenating the 2,6-diamino-3,5-dinitrotoluene by contacting the reaction mixture formed in step (f) with hydrogen at a pressure in the range of about 0.31 to about 3.45 MPa and a temperature in the range of about 20° C. to about 100° C. for sufficient time to hydrogenate the 2,6-diamino-3,5-dinitrotoluene, thereby producing 2,3,5,6-tetraminotoluene;
    h) contacting the 2,3,5,6-tetraminotoluene produced in (g) with an aqueous solution comprising 1 to 6 equivalents of acid per mol of 2,3,5,6-tetraminotoluene, optionally heating the solution, thereby dissolving the 2,3,5,6-tetraminotoluene;
    i) filtering the reaction mixture, thereby removing the spent hydrogenation catalyst;
    j) forming and precipitating the salt by adding an acid to the filtered reaction mixture, and
    k) cooling, filtering, and washing the precipitated 2,3,5,6-tetraminotoluene salt.

2. The process of claim 1 wherein the acid in steps (h) and (j) is selected from the group consisting of HCl, acetic acid, $H_2SO_4$, and $H_3PO_4$.

3. The process of claim 1 wherein Z=Cl and the acid in steps (h) and (j) is HCl.

4. The process of claim 1 wherein the glycol used in step (e) is distilled and recycled.

5. The process of claim 1 wherein the spent hydrogenation catalyst of step (i) is recovered and recycled.

6. The process of claim 1 wherein, in step (k), the precipitated salt is washed with water and methanol, and the methanol is recycled.

7. The process of claim 1 further comprising drying the 2,3,5,6-tetraminotoluene salt.

8. The process of claim 1 further comprising the addition of an aliphatic alcohol co-solvent in step (h).

* * * * *